United States Patent [19]

Ollmar

[11] Patent Number: 5,353,802
[45] Date of Patent: Oct. 11, 1994

[54] DEVICE FOR MEASUREMENT OF ELECTRICAL IMPEDANCE OF ORGANIC AND BIOLOGICAL MATERIALS

[75] Inventor: Stig Ollmar, Huddinge, Sweden

[73] Assignee: Centrum för Dentalteknik och Biomaterial, Huddinge, Sweden

[21] Appl. No.: 39,361

[22] PCT Filed: Oct. 18, 1991

[86] PCT No.: PCT/SE91/00703
§ 371 Date: Apr. 16, 1993
§ 102(e) Date: Apr. 16, 1993

[87] PCT Pub. No.: WO92/06634
PCT Pub. Date: Apr. 30, 1992

[30] Foreign Application Priority Data
Oct. 18, 1990 [SE] Sweden .............. 9003336-6

[51] Int. Cl.⁵ .............................................. A61B 5/05
[52] U.S. Cl. ................................................. 128/734
[58] Field of Search ............... 128/734–735, 128/741, 632, 635–636, 639, 642–644

[56] References Cited

U.S. PATENT DOCUMENTS

| | | |
|---|---|---|
| 3,866,600 | 2/1975 | Rey .................................. 128/734 |
| 4,540,002 | 9/1985 | Atlas . |
| 4,951,683 | 8/1990 | Davis . |

FOREIGN PATENT DOCUMENTS

| | | |
|---|---|---|
| 0314088A3 | 5/1989 | European Pat. Off. . |
| 0315854A1 | 5/1989 | European Pat. Off. . |

*Primary Examiner*—Angela D. Sykes
*Attorney, Agent, or Firm*—Jeffrey Slusher

[57] ABSTRACT

A device and method for noninvasive depth-selective detection and characterization of surface phenomena in organic and biological material such as tissues by surface measurement of the electrical impedance of the material. The device includes a probe with a plurality of measuring electrodes separated by a control electrode. Measuring equipment measures impedance in a desired frequency range. An adjustable amplifier maintains a chosen control signal derived from the potential of one of the measuring electrodes at the control electrode without loading the measuring electrode. Depth selectivity is achieved by controlling the extension of the electric field in the vicinity of the measuring electrodes by the control electrode actively driven with the same frequency as the measuring electrodes.

17 Claims, 6 Drawing Sheets

S-S

FIG. 3a
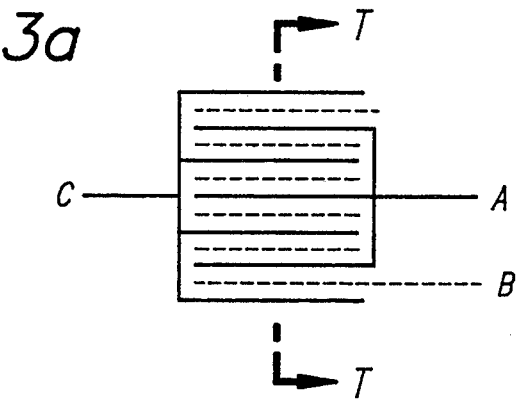
FIG. 3b
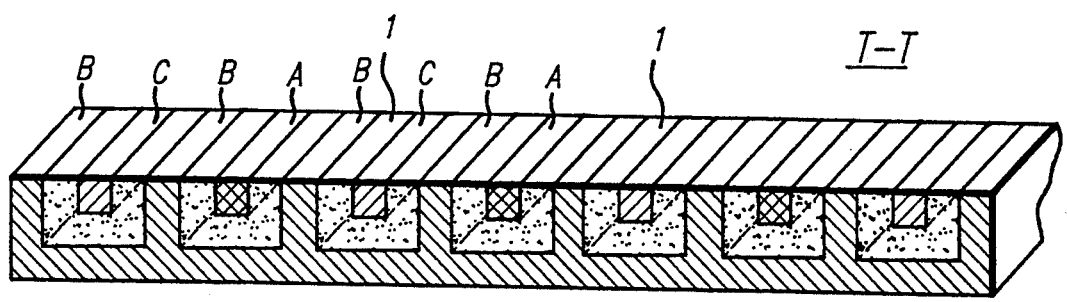
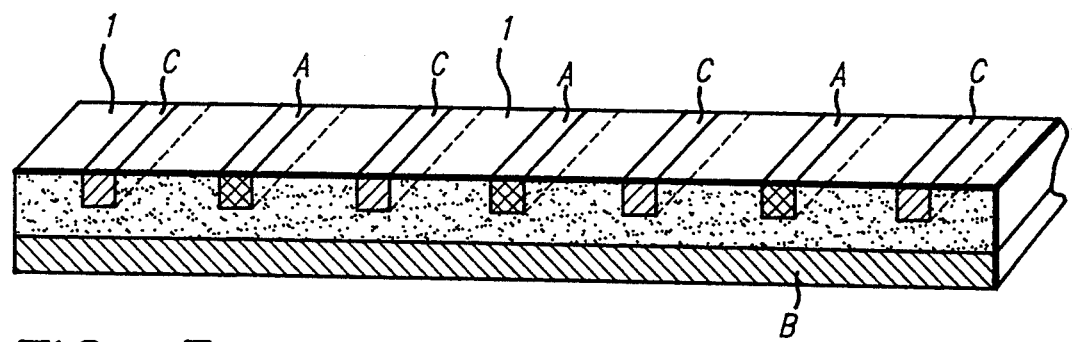
FIG. 3c

S-S

DEVICE FOR MEASUREMENT OF ELECTRICAL IMPEDANCE OF ORGANIC AND BIOLOGICAL MATERIALS

BACKGROUND OF THE INVENTION

The present invention relates to a device for non-invasive depth-selective detection and characterization of surface phenomena in organic and biological systems such as tissues by surface measurement of the electrical impedance of said material with said device as well as a method for said surface characterization.

Electrical impedance is a very sensitive indicator of minute changes in organic and biological material and especially tissues such as mucous membranes, skin and integuments of organs, including changes due to irritation caused by different reactions, and scientists all over the world have worked hard to find a convenient way to measure variations and alterations in different kinds of organic and biological material to be able to establish the occurrence of such alterations which are due to different states, characteristic of irritations from e.g. diseases.

Much of the fundamental knowledge within the current area stems from the field of electrochemistry. Potentiostats have for a long time been in use for studies of e.g. corrosion, and AC (alternating current) methods have gradually evolved and are well documented, cf. Claude Gabrielli: Identification of electrochemical processes by frequency response analysis. Solartron Instruments technical report number 004/83, 1984 and F. B. Growcock: What's impedance spectroscopy. Chemtech, September 1989, pp 564–572.

Excellent tools for work in this field are available, e.g. the 1286 Electrochemical Interface, Solartron Instruments, UK and the Model 378 Electrochemical Impedance Systems, EG&G Princeton Applied Research, N.J., U.S.A.

Characteristic features of these systems are that they are intended for use with specimens mounted in appropriate electrochemical cells.

It is well known that certain parameters in living tissues are reflected by electrical impedance of said tissues: U.S. Pat. No. 4,038,975 (Aug. 2, 1977) to Vrana et al. relates to an electrically instrumented method of diagnosing the presence of a neoplast in mucuos membrane samples wherein the electrical impedance of the sample has resistive and capacitive components and wherein the relative values of said components are indicative of the presence or absence of said neoplast by associating the sample with the terminals of a series circuit including in succession a grounded, amplitude-modulated high-frequency generator and first and second equal-valued resistors wherein the impedance of the generator and the resistance of both resistors are low relative to the impedance of the sample. Said association being made by connecting a test spot on the sample to the terminal of the second resistor remote from the junction of the first and second resistors and by connecting the bulk of the sample to the grounded terminal of the generator, simultaneously measuring the amplitudes of the potentials of the test spot and of the junction of the first and second resistors with respect to a reference value established at the junction of the generator and the first resistor, and computing from the measured values and from the reference value the resistive and capacitive portions of the impedance of the test spot.

By EP 0 315 854 (Appln. No. 88118083.0) to Honna is previously known a method and a system for measuring moisture content in skin by passing "weak" low frequency electric current through the keratinous layer between two electrodes abutted upon the skin, amplifying the electric voltage appearing on the layer, rectifying and taking out signals of the amplified output, and measuring the amplitude of the signal, which is characterized in that the voltage appearing on the keratinous layer is the voltage appearing between either one of said two electrodes whichever is closer to another electrode which is abutted upon said skin at a location outside said two electrodes.

The system comprises a measuring electrode structure of triple concentric circles including a central electrode, an intermediate electrode and an outer electrode all of which can be abutted on the skin, a generator which uses one of said electrodes as a common electrode and supplies low frequency signal between this common electrode and another of said three electrodes; an amplifier which converts the resulting current into a voltage appearing between said common electrode and yet another of said three electrodes, and a means to display the output voltage of the amplifier which is characterized in that a circuit means is provided for switching between a first circuit using said intermediate electrode as common electrode and a second circuit which uses the outer electrode as a common electrode.

Further prior art is disclosed in e.g. Yamamoto, T. & Yamamoto, Y.: Analysis for the change of skin impedance. Med. & Biol. Eng. & Comp., 1977, 15, 219–227; Salter, D. C.: Quantifying skin disease and healing in vivo using electrical impedance measurements. In: Non-invasive physiological measurements, Vol 1, 1979, Peter Rolfe ed., pp 21–64; Leveque, J. L. & De Rigal, J.: Impedance methods for studying skin moisturization. J. Soc. Cosmet. Chem., 1983, 34, 419–428; and Morkrid, L. & Qiao, Z.-G.: Continuous estimation of parameters in skin electrical admittance from simultaneous measurements at two different frequencies. Med. & Biol. Eng. & Comp., 1988, 26, 633–640.

Characteristic of existing technology in this field is that either:
 a) a biopsy would have to be excised in order to well define the actual tissue under test, i.e. not suitable for in vivo measurements; or
 b) electrodes are applied to the skin at separate sites, directing the electric test current right through the skin and regarding the inner part of the skin and deeper lying tissue as an almost ideal short circuit between the contact sites, i.e. no discrimination between the layers of the rather complicated anatomy of the skin.

There are devices for measuring the water content in the outermost layers of the skin (such as the Corneometer CM820PC, Courage+Khazaka Electronic GmbH, FRG) using interdigitated electrode patterns. A device called DPM9003 from NOVA Technology Corporation, Mass., U.S.A. employs a simple coaxial electrode. These devices have no means for controlling the measurement depth except for the limitations set by physical size. Indeed, they are applications of the well known principle of moisture measurement using fringing fields (Giles: Electronic sensing devices, Newnes, London, 1966/68, pp 80–81).

A device for measuring conductance of the fluids in mucous membranes of the airways has been published (Fouke, J. M. et al: Sensor for measuring surface fluid conductivity in vivo. IEEE Trans. Biomed. Eng., 1988, Vol 35, No 10, pp 877-881). This paper shows, backwards, the problem encountered while measuring on wet surfaces without a control electrode to enforce depth penetration.

It is possible to use Applied Potential Tomography/Electrical Impedance Tomography to obtain tomographic images of e.g. thorax or gastric regions, employing a large number of electrodes around the body and computing with reconstruction algorithms an image representing changes of conductivity in the body (Seagar, A. D. & Brown, B. H.: Limitations in hardware design in impedance imaging. Clin. Phys. Physiol. Meas., 1987, Vol. 8, Suppl. A, 85-90).

According to the present invention depth selectivity is achieved by controlling the extension of the electric field in the vicinity of the measuring electrodes by means of a control electrode between the measuring electrodes, the control electrode being actively driven with the same frequency as the measuring electrodes to a signal level, taken from one of the measuring electrodes but also multiplied by a complex number, in which the real and imaginary parts are optimized for each application depending upon the desired depth penetration. The function of the controlling field is analogous to that of a field effect transistor, well known from solid state physics. In biological tissue or "wet state", conduction mechanisms are complicated involving a number of ions, polarization effects, charged or polarizable organelles, etc. However, no reconstruction algorithms are needed to achieve depth selectivity, although consecutive measurements at different depths must be recorded in order to obtain a profile.

The principle is basically frequency independent, and works from DC to several MHz. Simple impedance measurements at one or a few frequencies, as well as impedance spectroscopy in this range can thus be done depth selective on e.g. skin.

In mucous membranes the fluid on the surface would normally short circuit measuring electrodes placed on the same surface; however, by use of the control electrode the test current is forced down into the mucous membrane rather than taking the shortest way and local definition of the actual tissue under test is thus achieved. These advantages are directly applicable while measuring impedance as an indicator of irritation during tests of irritants on skin and oral mucous membranes. It was also possible to measure impedance on kidneys while at the same time measuring the blood pressure within the kidney in the main artery, and it was found that impedance descriptive parameters correlated well with blood pressure. This opens the possibility to measure pressure, as well as microcirculation non-invasively in many organs during surgery by applying a probe to the surface of the organ. Another application is the measuring of pressure in the eye (diagnosis of glaucoma).

SHORT DESCRIPTION OF THE DRAWINGS

FIG. 2b is a cross-sectional view along plane S—S of FIG. 2a;

FIG. 3a is a cross-sectional view of a probe with linear, iterated structure;

FIG. 3b is a perspective view of the tip of the probe with a linear, iterated structure, electrically equvivalent to FIG. 3a;

FIG. 3c is a perspective view of the tip of a simplified structure of a similar arrangement, sufficient in some applications.

DESCRIPTION

The essential features of the invention are a probe with two measuring electrodes separated by a control electrode, suitable equipment for measuring the electric impedance in the desired frequency range, and an amplifier with adjustable amplification capable of maintaining the chosen control signal, derived from the potential of one of the measuring electrodes at the control electrode without loading said measuring electrode, i.e. the amplifier must have high input impedance and low output impedance in the frequency range used. The control electrode is following the potential of one of the measuring electrodes by multiplying the signal of the amplifier with a complex number in which the real and imaginary parts are optimized for each application. With the amplification factor set to zero, the system assumes the special case of signal ground at the control electrode. In this special case the system behaviour is similar to the system in the prime case of FIG. 1 described in the EP Publication No. 0 315 854 (Application No. 88118083.0), where one electrode is always connected to signal ground. However, the intermediate electrode of said system is not actively driven by an amplifier as in the present invention but is galvanically connected to signal ground. According to the present invention any control signal different from zero (the amplitude may be less than, equal to, or larger than the amplitude supplied to the measuring electrodes) will modify the depth penetration within a range determined by the shapes, sizes and distances of the electrodes and the properties of the tissue under test. The present amplifier of course can also be set to signal ground whereby the function signalwise corresponds to the previously known apparatus. However, said feature is outside the scope of the present invention.

The electrodes may be configured in concentric, linear, iterated linear or any topological way compatible with the essential features. Additional electrodes carrying guard, signal ground, driven guard, etc. may be required to optimize operation depending on the application. Cabling and shielding must be in accordance with established engineering practice in order to minimize electromagnetic interference. For use on humans, design may have to conform to local safety regulations.

It is important to limit excitation amplitude in order to minimize non-linearities inherent in living tissues. The amplitude supplied to the electrodes should be no more than a few tens of millivolts, preferably below 50 millivolts and more preferably about 25 millivolt. Higher amplitudes produce unreliable results. Working on wet mucous membranes does not require any special preparations. If deeper layers of the skin (stratum corneum and down) are to be investigated, the dry surface of the skin is preferably inundated with a salt solution of physiological concentration.

Figure 9A:
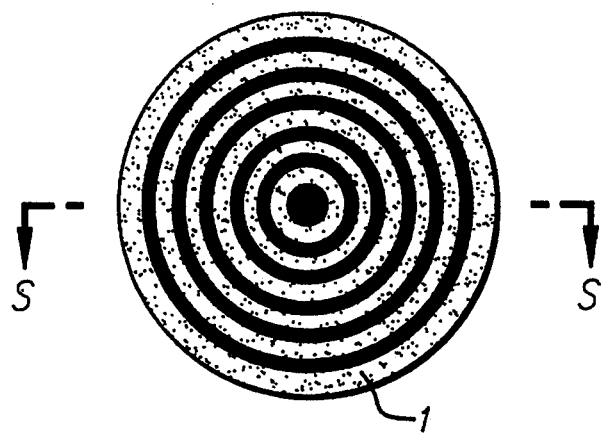
FIG. 9a is a plane topview of a generalized probe switchable into different configurations.
Figure 9B:
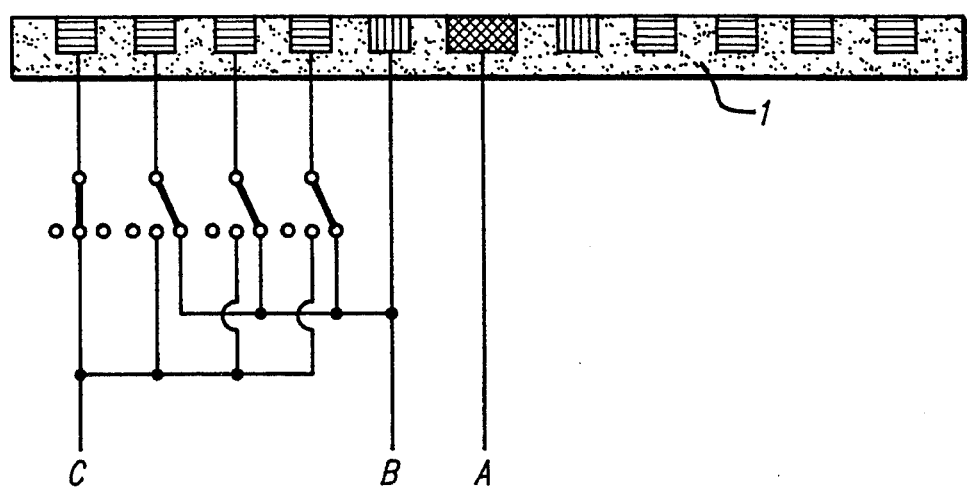
FIG. 9b is a cross-sectional view along plane S—S of FIG. 9a showing also switchable electrical pathways.

The capability of the control electrode to vary depth penetration is, as stated above, limited by the shapes, sizes and distances of the electrodes as well as the properties of the tissue under test. For a large range of depths a variety of probes of different sizes may thus seem necessary. However, a generalized probe can be achieved by adding a number of electrodes which are switched into different functions according to FIG. 9b. The dominating factor determining depth penetration is distances between electrodes; the basic theory has been expanded by Roy et al (Roy, A. & Apparao, A.: Depth of investigation in direct current methods. Geophysics, Vol. 36, No. 5, 1971, pp 943–959; Roy, K. K. & Rao, K. P.: Limiting depth of detection in line electrode systems. Geophysical Prospecting, 25. 1977, pp 758–767) for a number of electrode configurations.

It is, of course, still essential that the path of the measured test current is kept from the immediate surface of the probe by driving the virtual control electrode according to the present invention. When choosing a certain pair of measurement electrodes, i.e. the center electrode and the most distant of the activated rings, all (minimum one) electrodes in between are connected together to form the virtual control electrode. Distances between electrodes may be the same or vary in a non-linear way to achieve e.g. stepwise increase of penetration with a fixed factor. With the generalized probe coarse depth penetration is thus selected by switching electrodes of the probe, and fine adjustment of penetration as well as facilitating measurements on wet surfaces are achieved by driving the virtual control electrode to the proper potential. The switches may be mechanical or electronic and may be manually operated or under computer control.

For achieving maximum penetration depth, the best mode is thus to use the center electrode and outermost ring as measurement electrodes and using the rings in between, connected together, as a control electrode, and driving this virtual control electrode with a potential derived from the potential of one of the measurement electrodes in the same way as described above.

If the application is such that optimum results would come from a lesser depth penetration, the best mode would be to use another ring as one of the measurement electrodes, leaving the outer ring or rings unconnected and using the ring or rings between the outer electrode and selected second electrode, connected together, as the control electrode.

PREFERRED EMBODIMENT

Figure 1:
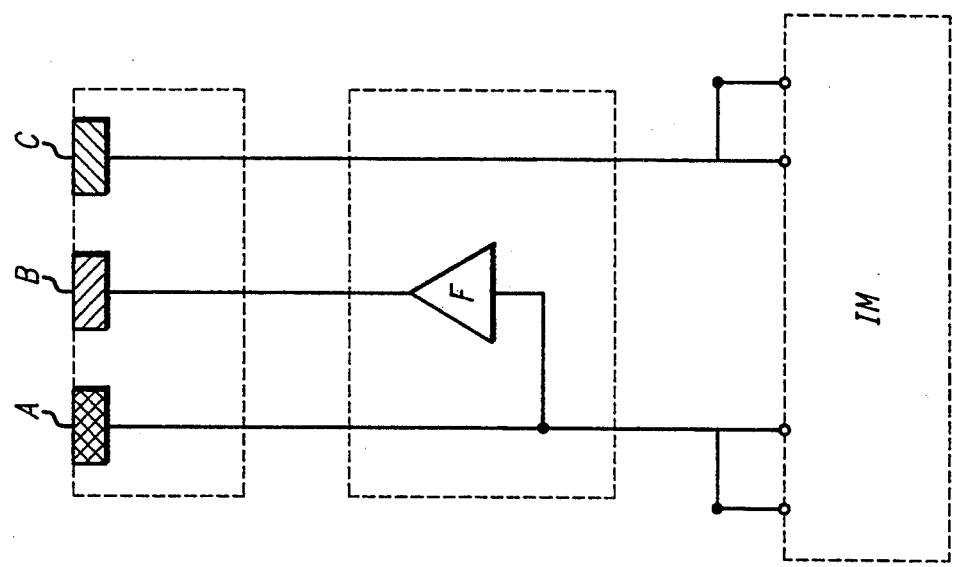
FIG. 1 is a block diagram illustrating the principle of measurement employed in an embodiment of the present invention.

In FIG. 1 is shown a block diagram illustrating the principle of measurement employed in a preferred embodiment of the present invention. Two measuring electrodes A and C are separated by a third electrode, the control electrode B. Control electrode B will be actively held at a given potential by a controllable amplifier F, amplifier F also receiving an input reference signal from electrode A using a high impedance input terminal and supplying said control electrode B via a low impedance output terminal so that said control electrode B will track said electrode A but with a signal level ensueing from the transfer function of the amplifier F. Measuring electrodes A and C are connected to a standard instrument for impedance measurement IM.

Figure 2A:
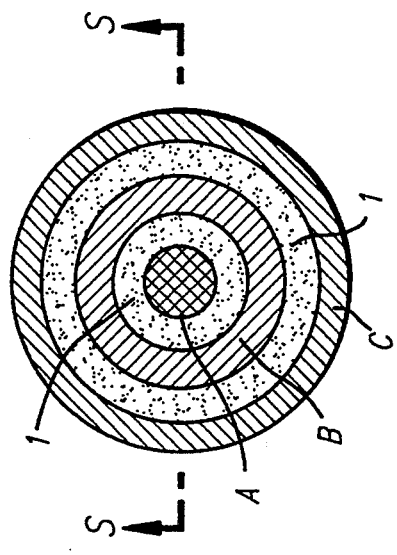
FIG. 2a is a plane topview of the tip of a probe with two measuring electrodes separated by a control electrode.
Figure 2B:
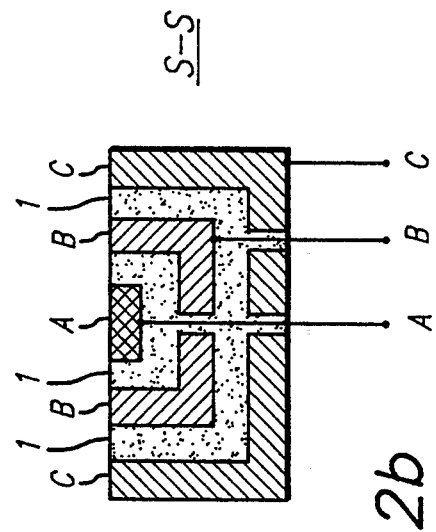

FIG. 2a and FIG. 2b illustrates a preferred embodiment of the tip end of a measurement probe for studies of irritation on i.e. oral mucosa and skin. Said probe consists of the electrodes A, B and C, each electrically isolated from the other, in a coaxial arrangement and presents as depicted in FIG. 2a, a plane surface containing respective electrodes A, B and C and the isolating material 1.

FIG. 3b and FIG. 3c are showing the respective embodiments of an open linear, iterated structure which can be used according to the invention. The structure of FIG. 3c involves a simplified feature, within the scope of the invention sufficient in some applications.

The invention relates to a device for depth-selective, non-invasive, local measurement of electric impedance in tissues such as preferably skin, mucous membranes and integuments of organs in or from humans or animals in vivo or in vitro comprising a probe with concentric electrodes, the size of which is depending upon desired maximum depth penetration. The electrodes comprise a central electrode being one of two measuring electrodes, and the central electrode being surrounded by a control electrode which is following the potential of the central electrode by multiplying the signal of one of the measuring electrodes by a complex number in which the real and imaginary parts are optimized for each application. The control electrode is surrounded by a second measuring electrode. The essential part of the probe, except for the contact surface, is surrounded by conductive material at signal ground or following the potential at the central electrode by a factor of one. All conductive parts are separated by stable isolating material and all electrodes and isolating material on the contact surface arranged in one plane, concave or convex surface to fit the surface of the test site with minimum liquid wedge. The device is further provided with suitable equipment for measuring impedance at a limited number of frequencies, these frequencies determined in pretests for a certain application by a wide scan of frequencies and plotting of Nyquist or Bode graphs.

For measurement of irritation, impedance values at two frequencies, one in the range several hundred kHz to several Mhz, and one in the range 1 kHz to 100 kHz, will work. The major information comes with the lower frequency, the impedance at the higher frequency is used to normalize the geometrical definition of the tissue under test. For convenience, an irritation index defined as the quotient between the absolute value at 20 kHz and the absolute value at 1 MHz has been introduced. Phase is not included in this irritation index. See FIG. 4: SIMPLE IRRITATION MODEL. A decrease in irritation index means increased irritation.

For depth selectivity the signal of the control electrode is optimized when the real part is a number between 0.01–10 and the imaginary part as close to zero as possible for the transfer function of the amplifier F in the used frequency range.

APPLICATIONS

SIMPLE IRRITATION MODEL, FIG. 4

Figure 4A:
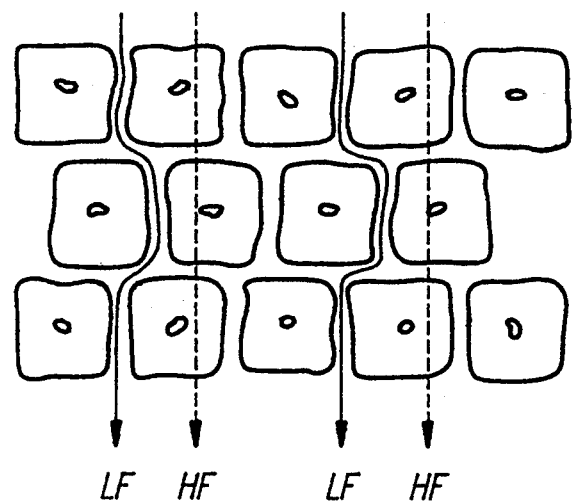
FIG. 4a is an illustration of a normal tissue with closed packed cells.

FIG. 4a shows normal tissue with close packed cells.

Figure 4B:
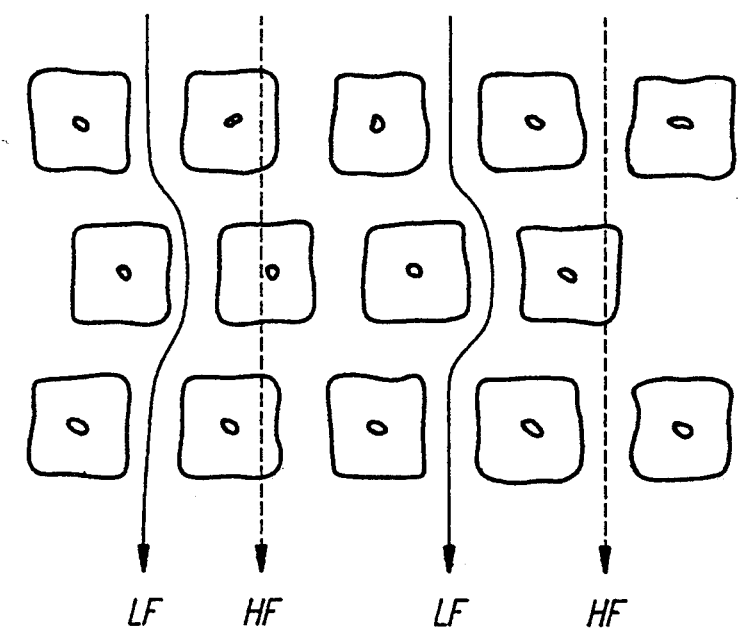
FIG. 4b is an illustration of an irritated tissue showing increased intercellular space.
Figure 5:
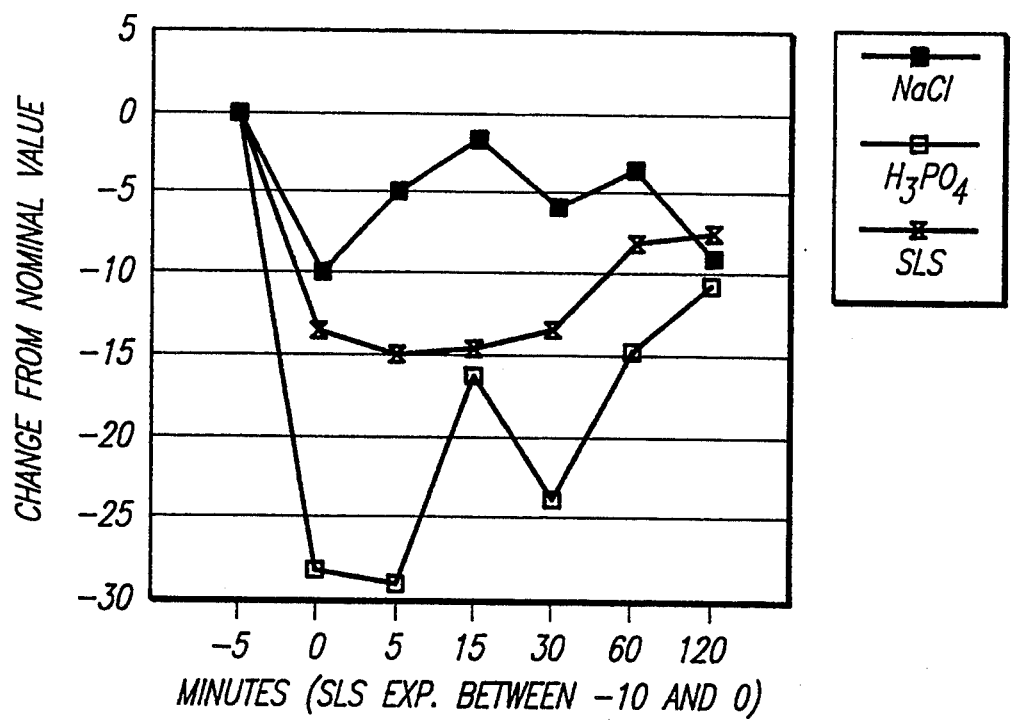
FIG. 5 is a plot showing mean values in % obtained with prior technique in measurement of irritation on oral mucosa for NaCl, $H_3PO_4$, SLS.
Figure 6:
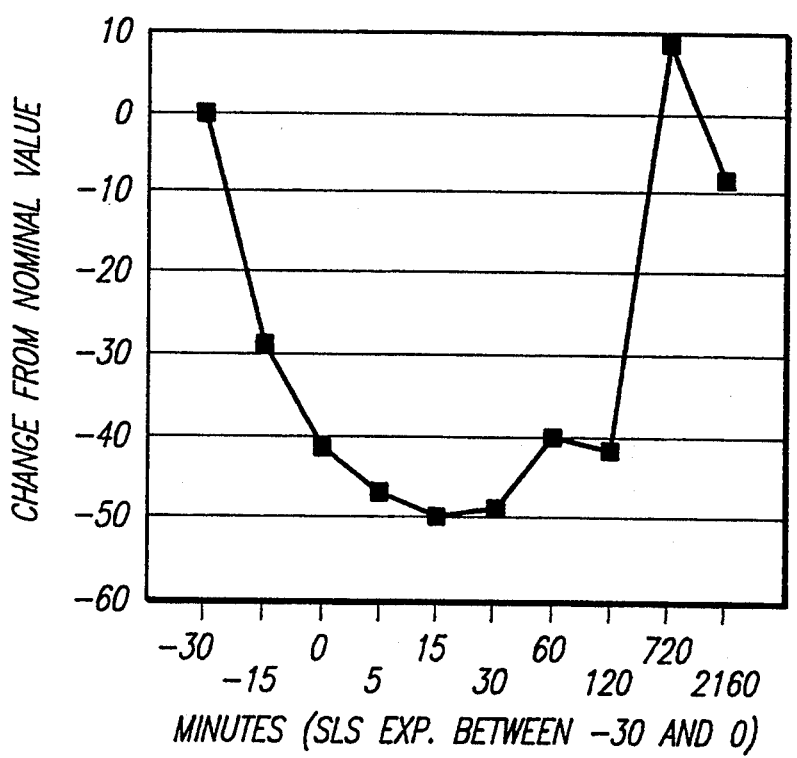
FIG. 6 is a plot showing values in % for one person obtained with the technique according to the invention in the measurement of irritation on oral mucosa.

FIG. 4b shows irritated tissue with increased intercellular space.

High frequency (HF) is coupled capacitively through cell membrane to cell interior.

Low frequency (LF) is confined to extracellular/intercellular space.

Conductivity is essentially the same in intra- or extracellular liquid.

IRRITATION ON ORAL MUCOSA, FIG. 5.

Prior Technology

Ten voluntary test persons were exposed to three different liquid substances (sodium chloride, sodium lauryl sulphate and phosphoric acid). Exposure time was 5 minutes for NaCl and $H_3PO_4$ (−5 to 0 in graph) and 10 minutes for SLS (however plotted between −5 and 0 in graph, for uniformity of nominal value). Electrical impedance was measured through the cheek, with a small electrode on the inside of the cheek at the site of irritation, and a large electrode on the outside of the cheek, thus creating a conical field yielding highest electric current density at the inside. Impedance information is thus dominated by events at the inside, however somewhat occluded by artifacts occurring in intercepted regions of muscular tissue and skin. Not suitable for diagnostic purposes, since averages from a number of test persons are necessary to obtain significant results.

With the method impedance from the skin of the cheek as well as muscular layers are involved, and averages of data from ten or more test persons are required to see any significant changes, i.e. the prior method is not suitable for diagnostic purposes, and indeed not many mucous membranes are available from two sides non-invasibly.

IRRITATION ON ORAL MUCOSA, FIG. 6.

According to the invention

By the measurement according to the invention artifacts from muscular tissue and skin are eliminated, since the device measures to a controlled depth of the oral mucosa. The results are stable and it is easy to follow the course of events on one single person, i.e. the method is well suited for diagnostic purposes. The graph shows result from 30 minutes exposure (−30 to 0 in graph) to sodium lauryl sulphate, with a pause of approximately 15 seconds half way (at −15 in graph) to measure that point. After 12 hours irritation index is back at normal levels. Maximum irritation of this substance on this test person was reached 15 minutes after cessation of exposure.

With the device according to the invention it is possible to measure non-invasively from the surface of any mucous membrane which can be reached from one side. In the case of oral mucosa, artifacts from skin or muscular tissue are eliminated, and it is possible to follow irritation processes on single persons with high accuracy.

IRRITATION ON SKIN, FIG. 7.

According to the invention

Figure 7:
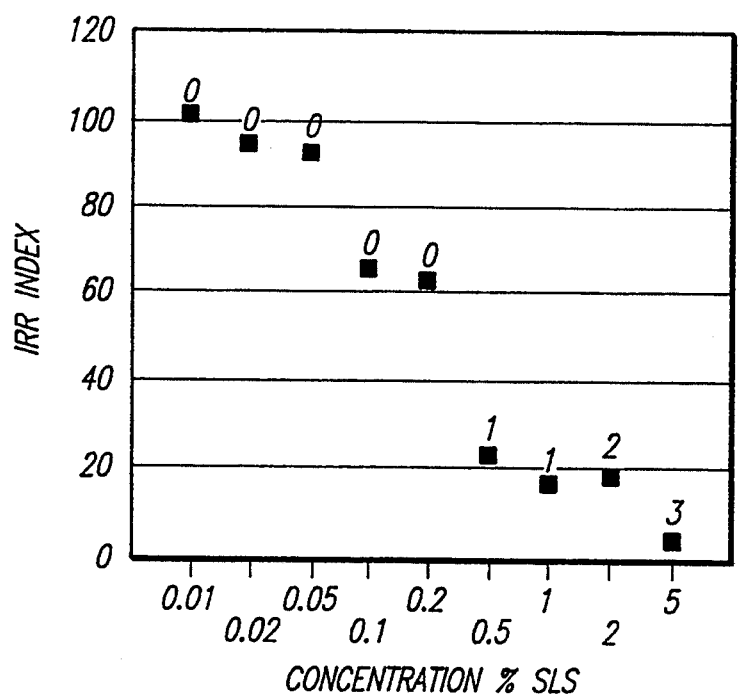
FIG. 7 is a plot showing irritation index results of measurement of irritation on skin with the technique according to the invention for one person with 20 hours of exposure of material and additionally 24 hours.

Voluntary test persons were exposed to patch test on back. Sodium lauryl sulphate of different concentrations was applied for 24 hours in Finn chambers. Irritation was measured according to the invention and assessed according to standard procedures by a trained dermatologist (scale 0..3, interior labels in graph). There is good correlation between irritation index and concentration for all concentrations, despite the fact that the trained dermatologist could not discern any irritation at the lower concentrations (marked 0 in the graph). With the claimed invention it was possible to detect irritation effects not visible to a trained dermatologist (points marked 0 in FIG. 7).

PRESSURE IN KIDNEY IN VIVO, FIG. 8.

According to the invention

Absolute value of electrical impedance at 20 kHz was measured on the intact surface of a rat kidney, still in function. At the same time arterial pressure was measured with a sensor implanted in the supporting vessel. Consecutive blood pressures were induced by choking and releasing the supporting artery. Impedance correlated well with pressure, with a delay of approximately 15 seconds. Graph shows sequence of events. Autoregulatory mechanisms of the kidney are not demonstrated explicitly with this type of plot.

Figure 8:
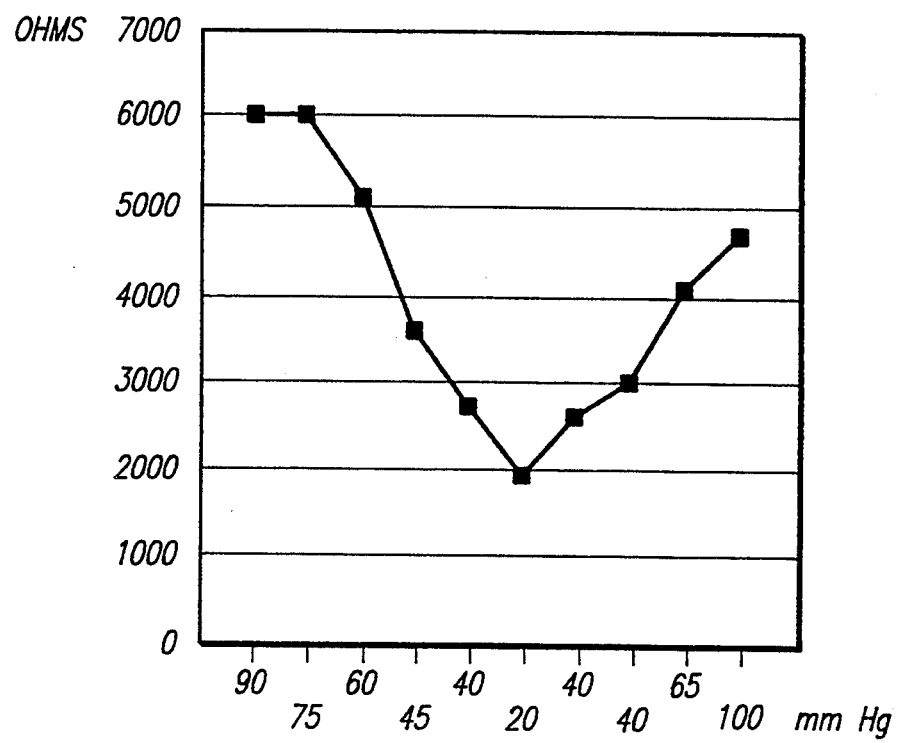
FIG. 8 is a plot showing absolute value of electrical impedance at 20 kHz measured on intact surface of rat kidney at consecutive values of blood pressure by stepwise choking and releasing supporting artery in vivo.

The device according to the invention has been tried for measurement of electric impedance on intact kidney of rat in vivo, the kidney being exposed to changes in blood circulation and pressure. There is significant correlation between pressure and value of measured impedance, the correlation being higher at 20 kHz (FIG. 8) than at 100 kHz. Thus, the device according to the invention may be useful to detect ischemic states during e.g. transplantational surgery.

As the behaviour of the eye seems similar to the kidney when it comes to tissue changes in the surface due to internal pressure, the invention may be useful for diagnosis of glaucoma.

I claim:

1. A device for depth-selective measurement of electrical impedance in a test portion of organic or biological materials comprising:

a probe having a plurality of measuring electrodes and a control electrode located between at least two of the measuring electrodes, one of the measuring electrodes also forming a predetermined reference electrode;

voltage and impedance measuring means for applying electrical potential over the measuring electrodes and for measuring electrical impedance of the test portion between the measuring electrodes; and an amplifier that has a high-impedance input that is electrically connected to the reference electrode, the reference electrode remaining substantially unloaded by the amplifier, the amplifier also having a low-impedance output that is electrically connected to the control electrode;

an electric control field being adapted to extend from the control electrode into the test portion; and a dynamic electrical potential of the control electrode being maintained during impedance measuring of the test portion.

2. A device as defined in claim 1, in which the amplitude of the electrical potential applied over the measuring electrodes is no more than 50 millivolts.

3. A device as defined in claim 2, in which the amplitude of the electrical potential applied over the measuring electrodes is no more than 25 millivolts.

4. A device as defined in claim 1, further including control means for varying a transfer function of the amplifier with respect to both gain and phase.

5. A device as defined in claim 4, in which a gain of the amplifier is variable within the range 0.01 to 10.00 and corresponds to a desired field penetration depth and the phase of the amplifier is set at a minimum phase value.

6. A device as defined in claim 1, said probe having a contact surface and said device further including:
   electrically insulating material between the measuring electrodes and the control electrode;
   the measuring electrodes, the control electrode and the insulating material being flush with one another at the contact surface;
   whereby:
   any residual liquid layer between the probe and the test portion during operation of the device is minimized.

7. A device as defined in claim 6, further including a conductive shield surrounding the probe except for the contact surface and maintained at the potential of the control electrode.

8. A device as defined in claim 1, in which the voltage and impedance measuring means applies the electrical potential over the measuring electrodes at a first and a second frequency for measurement of irritation impedance values in the test portion.

9. A device as defined in claim 8, in which the first frequency is greater than 100 kHz and the second frequency is less than 100 kHz, the electrical potential when at the first frequency forming a normalizing signal corresponding to the geometry of the test portion.

10. A device as defined in claim 1, in which the voltage and impedance measuring means further measures impedance at a predetermined number of predetermined frequencies.

11. A device as defined in claim 1, in which the measuring electrodes and the control electrode are substantially annular and concentric and are separated by an insulating material.

12. A device as defined in claim 1, in which the distance between the control electrode and each respective one of the measuring electrodes is substantially equal to a respective one of a predetermined number of penetration depths.

13. A device as defined in claim 12, in which:
the number of measuring electrodes is greater than two, with a predetermined one of the measuring electrodes forming a primary measuring electrode and with the remaining measuring electrodes forming switchable electrodes; and
further including depth selection means for electrically connecting and disconnecting selected ones of the switchable electrodes to each other and to the control electrode.

14. A method for depth-selective, non-invasive characterization of a test portion of organic and biological materials, comprising the following steps:
   A) applying to a test surface of the test portion a probe that includes a plurality of measuring electrodes and a control electrode located between at least two of the measuring electrodes, one of the measuring electrodes also forming a predetermined reference electrode;
   B) applying electrical voltage to the measuring electrodes;
   C) applying a variable voltage to the control electrode with a predetermined phase shift and non-zero amplitude gain relative to the electrical voltage of a predetermined one of the measuring electrodes; and
   D) measuring electrical impedance of the test portion between the measuring electrodes.

15. A method as defined in claim 14, further including the steps of varying the voltage applied to the control electrode until the phase shift achieves a minimum and setting the predetermined phase shift to the minimum.

16. A method as defined in claim 14, further including the following steps:
   A) measuring impedance values in the test portion by applying voltage to the measuring electrodes sequentially at a plurality of frequencies, including a first frequency, which forms a normalization frequency, and a second frequency, which is lower than the first frequency; and
   B) calculating an irritation impedance value as a predetermined function of the measured impedance values at the plurality of frequencies.

17. A method as defined in claim 14, further including the following steps:
   A) determining a desired measurement electric field depth; and
   B) changing the distance between the control electrode and selected ones of the measuring electrodes to correspond to the desired measurement electric field depth by selectively switching the selected measuring electrodes into electrical contact with the control electrode.

* * * * *